United States Patent
Mun et al.

(10) Patent No.: US 9,500,599 B2
(45) Date of Patent: Nov. 22, 2016

(54) SURFACE INSPECTION APPARATUS FOR SEMICONDUCTOR CHIPS

(71) Applicant: Samsung Electronics Co., Ltd., Suwon-si (KR)

(72) Inventors: Youn-Jo Mun, Cheonan-si (KR); Hoon Sohn, Daejeon (KR); Sang-Young Kim, Asan-si (KR); Yun-Kyu An, Daejeon (KR); Sung-Il Cho, Asan-si (KR); Seung-Weon Ha, Cheonan-si (KR); Jin-Yeol Yang, Daejeon (KR); Soon-Kyu Hwang, Daejeon (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 14/603,809

(22) Filed: Jan. 23, 2015

(65) Prior Publication Data

US 2015/0204800 A1 Jul. 23, 2015

(30) Foreign Application Priority Data

Jan. 23, 2014 (KR) ........................ 10-2014-0008579

(51) Int. Cl.
*G01N 21/95* (2006.01)
*G01J 5/10* (2006.01)
(Continued)

(52) U.S. Cl.
CPC ......... *G01N 21/9501* (2013.01); *G01J 5/0896* (2013.01); *G01J 5/10* (2013.01); *H04N 5/33* (2013.01); *G01J 2005/0081* (2013.01); *G01N 2201/06113* (2013.01)

(58) Field of Classification Search
CPC ........... G01N 25/72; G01N 2223/073; G01N 2223/40; G01N 2223/401; G01N 2223/427; G01N 2223/509; G01N 21/9501; G01N 2201/06113; G06T 2207/10048; G06T 2207/30148; H04N 5/33; G01J 2005/0077; G01J 2005/0081; G01J 5/0896; G01J 5/01
See application file for complete search history.

(56) References Cited

U.S. PATENT DOCUMENTS 5,156,461 A * 10/1992 Moslehi .................... G01J 5/00
250/338.1
5,255,286 A * 10/1993 Moslehi ................ G01J 5/0003
250/227.11
(Continued)

FOREIGN PATENT DOCUMENTS

EP 00983905 4/2000
JP 2004138442 5/2004
(Continued)

OTHER PUBLICATIONS

An, et al., Laser Lock-In Thermography for Detection of Surface-Breaking Fatigue Cracks on Uncoated Steel Structures, NDT&E International, vol. 65, Mar. 2014, pp. 54-63.
(Continued)

*Primary Examiner* — Marcus Taningco
(74) *Attorney, Agent, or Firm* — Onello & Mello, LLP

(57) ABSTRACT

A surface inspection apparatus and method of inspecting chip surfaces includes a laser generator that generates a periodic CW laser and is transformed into an inspection laser beam having a beam size smaller than a surface size of the chip. Thus, the inspection laser beam is irradiated onto a plurality of the semiconductor chips such that the semiconductor chips are partially and simultaneously heated. Thermal waves are detected in response to the inspection laser beam and thermal images are generated corresponding to the thermal waves. A surface image is generated by a lock-in thermography technique and hold exponent analysis of the thermal image, thereby generating surface image in which a surface defect is included. Time and accuracy of the surface inspection process is improved.

18 Claims, 8 Drawing Sheets

(51) Int. Cl.
*G01J 5/08* (2006.01)
*H04N 5/33* (2006.01)
*G01J 5/00* (2006.01)

(56) References Cited

U.S. PATENT DOCUMENTS

| | | | |
|---|---|---|---|
| 6,452,180 B1 | 9/2002 | Nistler et al. | |
| 6,704,435 B1 * | 3/2004 | Imaino | G01N 21/9506 382/108 |
| 6,943,353 B2 * | 9/2005 | Elmore | G01J 3/02 250/339.02 |
| 7,173,245 B2 * | 2/2007 | Shakouri | G01J 5/00 250/339.1 |
| 7,709,794 B2 * | 5/2010 | Zhao | G01N 25/72 250/334 |
| 7,961,763 B2 | 6/2011 | Furman et al. | |
| 7,966,883 B2 | 6/2011 | Lorraine et al. | |
| 8,377,624 B2 | 2/2013 | Jarek et al. | |
| 8,742,347 B2 * | 6/2014 | Altmann | G01N 1/00 250/332 |
| 9,025,020 B2 * | 5/2015 | Deslandes | G01N 25/72 348/92 |
| 2003/0179369 A1 * | 9/2003 | Feldman | G01N 21/8806 356/237.2 |
| 2010/0302360 A1 | 12/2010 | Arai et al. | |
| 2013/0250385 A1 * | 9/2013 | Wolters | G02B 27/1006 359/201.1 |
| 2013/0293879 A1 | 11/2013 | Honda et al. | |

FOREIGN PATENT DOCUMENTS

| | | |
|---|---|---|
| JP | 2005175101 | 6/2005 |
| JP | 2007108110 | 4/2007 |
| JP | 2011203245 | 10/2011 |
| KR | 200514424 | 2/2005 |
| KR | 201054516 | 5/2010 |
| KR | 201364275 | 6/2013 |
| WO | 0173819 | 10/2001 |
| WO | 2009073014 | 6/2009 |

OTHER PUBLICATIONS

An, et al., Laser Lock-In Thermography for Fatigue Crack Detection in an Uncoated Metallic Structure, Proceedings of SPIE, vol. 8692, ISBN: 9780819494757, on Apr. 26, 2013.

* cited by examiner

SURFACE INSPECTION APPARATUS FOR SEMICONDUCTOR CHIPS

CROSS-REFERENCE TO RELATED APPLICATIONS

This application claims benefit under 35 U.S.C §119 to Korean Patent Application No. 10-2014-0008579 filed on Jan. 23, 2014 in the Korean Intellectual Property Office, the disclosure of which is incorporated by reference herein in its entirety.

BACKGROUND

1. Field

Example embodiments relate to a surface inspection apparatus and method of inspecting surfaces of semiconductor chips using the same, and more particularly, to a non-destructive surface inspection apparatus for semiconductor chips and a method of inspecting surfaces of semiconductor chips non-destructively using the same.

2. Description of the Related Art

Various non-destructive inspection technologies have been suggested and used for surface inspection of semiconductor chips. However, the conventional non-destructive inspection apparatus usually requires a minimal defect size and the absence of foreign matter on a surface of the semiconductor chips for sufficient accuracy of the surface inspection. Particularly, when foreign matter is not sufficiently removed from the chip surface, the inspection accuracy is remarkably decreased. This can be the case even in a situation where a minimal amount of foreign matter is present.

In addition, the conventional non-destructive inspection is usually performed on each chip on a wafer sequentially, one-at-a-time. This necessarily requires a large amount of inspection time, which significantly reduces the overall manufacturing efficiency of the semiconductor chips. Particularly, as wafers continue to become enlarged in size and as the number of the chips on a single wafer also continues to increase, the surface inspection time for the chips is being rapidly increased. For that reason, the reduction of the surface inspection time becomes a significant factor for maintaining or improving manufacturing efficiency of the semiconductor chips.

Furthermore, an optical inspection technique, one of the most widely used non-destructive inspection techniques, is sensitive to the surface conditions of the chip and the presence of a minor amount of foreign matter on the surface tends to cause an inspection error and finally to interrupt the operation of the inspection apparatus, which results in a great increase of the inspection time for the semiconductor chips.

SUMMARY

Embodiments of the present inventive concepts provide for an improved surface inspection apparatus and method for reducing the inspection time together with high inspection accuracy and efficiency.

Example embodiments of the present inventive concepts provide a surface inspection apparatus for semiconductor chips in which a periodic continuous wave (CW) laser is irradiated to a chip surface and the lock-in amplitude images of the chip surface are generated in response to the CW laser, thereby increasing the inspection accuracy and sufficiently reducing the inspection time.

Example embodiments of the present inventive concepts further provide a method of inspecting surfaces of semiconductor chips using the above surface inspection apparatus.

According to an aspect of the present inventive concepts, there is provided an apparatus for inspecting surfaces of semiconductor chips including a laser generator generating a periodic continuous wave (CW) laser, a laser controller transforming the periodic CW laser into an inspection laser beam of which a beam size is smaller than a surface size of the semiconductor chip and irradiating the inspection laser beam onto a plurality of the semiconductor chips such that the semiconductor chips are partially and simultaneously heated by the inspection laser beam, a thermal image generator detecting thermal waves TW radiated from the semiconductor chips in response to the inspection laser beam and generating thermal images corresponding to the thermal waves, and a lock-in processor processing the thermal image using a lock-in thermography technique, thereby generating a lock-in thermography image of the thermal image in which a surface defect is included.

In an example embodiment, the laser generator may include a function generator generating a periodic waveform voltage in response to a trigger signal, a modulating driver amplifying the waveform voltage and converting the waveform voltage into a modulated current having a period of the periodic waveform voltage, and a laser oscillator oscillated by the modulated current thereby emitting the periodic CW laser modulated in accordance with the modulated current.

In an example embodiment, the periodic voltage may include a square waveform and the CW laser may be modulated by the periodic square waveform such that the semiconductor chip may undergo periodically repeated heating and cooling at each scanning point on a surface thereof.

In an example embodiment, the laser controller may include a beam expander expanding a bundle of rays of the CW laser thereby generating an expanded laser, a beam splitter splitting the expanded laser into a plurality of parallel spot beams as the inspection laser beam, and a position guider changing a relative position of the beam splitter with respect to a substrate on which a plurality of the semiconductor chips may be arranged. Each of the parallel spot beams may have a cross-sectional beam size smaller than a surface of the semiconductor chip and at least two parallel spot beams may be individually irradiated onto the surface of a single semiconductor chip. The position guider may change scanning points of the semiconductor chips to which the parallel spot beams are individually irradiated.

In an example embodiment, the beam splitter may include a plurality of beam passing holes through which the parallel spot beams may individually pass toward the substrate such that the cross-sectional beam size is controlled by a size of the beam passing hole.

In an example embodiment, a number of the beam passing holes may be three to five times of a number of the semiconductor chips on the substrate such that three to five parallel spot beams may be individually irradiated onto a single semiconductor chip.

In an example embodiment, the apparatus may further include a flat beam generator for converting a ray distribution of the expanded beam from a Gaussian distribution into a uniform distribution thereby generating a flat beam having a uniform intensity such that the parallel spot beams may have the uniform intensity.

In an example embodiment, the thermal image generator may include a base plate between the beam splitter and the substrate and having a plurality of penetrating holes, at least two parallel spot beams penetrating each of the penetrating holes, and a plurality of thermal image chips arranged on a surface of the base plate and detecting thermal waves radiated from the scanning points of the semiconductor chips, thereby generating the thermal images at each of the scanning points by a unit of the semiconductor chip.

In an example embodiment, the thermal wave may include infrared waves propagating from the scanning point with a Gaussian distribution and wherein the thermal image generator may include an infrared camera corresponding to the infrared waves.

In an example embodiment, the laser generator may include a line beam generator transforming the CW laser into a linear beam as the inspection laser beam, and a beam provider providing the linear beam to a plurality of semiconductor chips arranged in the longitudinal direction such that the linear beam may be simultaneously irradiated onto a plurality of scanning points of each semiconductor chip along the longitudinal direction. The linear beam may extend along a longitudinal direction of a substrate on which a plurality of the semiconductor chips may be arranged and having a beam width that is smaller than a surface size of the semiconductor chip.

In an example embodiment, the beam provider may include a Galbano mirror between the substrate and the line beam generator.

In an example embodiment, the thermal wave may include infrared waves propagating from the scanning point with a Gaussian distribution and the thermal image generator may include an infrared camera detecting the infrared wave and generating the thermal images corresponding to the infrared waves at each of the scanning points by a unit of the semiconductor chip.

In an example embodiment, the lock-in processor may include a lock-in amplitude processor processing amplitudes of the thermal waves to remove dummy images corresponding to dummy waves caused by thermal disturbances from the thermal images, thereby generating lock-in amplitude images corresponding to the thermal images for each scanning point as the lock-in thermography images.

In an example embodiment, the apparatus may further include an image processor processing the lock-in amplitude images, thereby generating a surface image of each of the semiconductor chips by which the surface defect is visually displayed.

In an example embodiment, the image processor may include a discontinuous image detector processing the lock-in amplitude image and detecting image singularities from the lock-in amplitude image, thereby generating a visually enhanced lock-in amplitude image in which discontinuous portions are visually shown on the lock-in amplitude image, and a noise filter removing noise from the visually enhanced lock-in amplitude image, thereby generating the surface image of the semiconductor chip.

In an example embodiment, the discontinuous image detector may include a holder exponent analyzer in which the image singularities may be detected through a holder exponent analysis process.

In an example embodiment, the apparatus may further include a main controller connected to the laser generator, the laser controller, the thermal image generator and the lock-in processor, wherein the main controller controls the laser generator and the thermal image generator to be synchronized with each other.

According to another aspect of the present inventive concepts, there is provided method of inspecting surfaces of semiconductor chips. A periodic continuous wave (CW) laser may be generated and may be transformed into an inspection laser beam of which a beam size is smaller than a surface size of the semiconductor chip. Then, the inspection laser beam may be irradiated onto a plurality of the semiconductor chips such that the surfaces of the semiconductor chips may be partially and simultaneously heated by the inspection laser beam. Thermal waves may be detected from the semiconductor chips in response to the inspection laser beam thereby generating thermal images corresponding to the thermal waves. The thermal image may be processed by using a lock-in thermography technique, thereby generating a lock-in amplitude image of the thermal image in which a surface defect is included.

In an example embodiment, the CW laser may be generated in a periodic square waveform and the thermal image is generated by every period of the CW laser.

In an example embodiment, a first control signal for generating the periodic CW laser is synchronized with a second control signal for generating the thermal images such that the thermal images are generated by every period of the CW laser.

In an example embodiment, the CW laser may be split into a plurality of parallel spot beams passing through a plurality of beam passing holes of a pattern mask and at least two parallel spot beams may be irradiated onto a surface of the semiconductor chip on condition that the parallel spot beams may be simultaneously irradiated to a plurality of the semiconductor chips that is arranged on a single substrate.

In an example embodiment, the CW laser may be transformed into a linear beam extending along a longitudinal direction of a substrate on which a plurality of the semiconductor chips may be arranged and having a beam width smaller than a surface of the semiconductor chip, and the linear beam may be simultaneously irradiated onto a plurality of scanning points of each semiconductor chip along the longitudinal direction.

In an example embodiment, a surface image visually displaying the surface defect may be further generated with respect to each of the semiconductor chips by processing the lock-in amplitude image.

In an example embodiment, the surface image may be generated as follows. The lock-in amplitude image may be processed by a holder exponent analysis technique to detect image singularities from the lock-in amplitude image, thereby generating visually enhanced lock-in amplitude image in which discontinuous portions may be visually shown on the lock-in amplitude image. Then, various noise may be removed from the visually enhanced lock-in amplitude image, thereby generating the surface image of the semiconductor chip.

According to another aspect of the present inventive concepts, an apparatus for inspecting surfaces of semiconductor chips, comprises: a laser unit that generates a plurality of periodic continuous wave (CW) inspection laser beams; a wafer carrier that positions a wafer having a plurality of chips in a path of the inspection laser beams, the plurality of inspection laser beams being arranged to simultaneously heat corresponding portions of the plurality of chips, the plurality of inspection laser beams each being of a cross-sectional area that is less than a surface area of individual ones of the chips; and a thermal image generator detecting thermal waves radiated from the chips in response to the inspection laser beams and generating thermal images corresponding to the thermal waves.

In an example embodiment, the laser unit comprises: a laser generator that generates a first periodic continuous wave (CW) inspection laser beams; and a laser controller that controls a transformation of the first inspection laser beam from a single laser beam to the plurality of inspection laser beam.

In an example embodiment, the apparatus further comprises a lock-in processor processing the thermal image using a lock-in thermography technique, thereby generating a lock-in thermography image of the thermal image in which a surface defect is included.

In an example embodiment, the apparatus further comprises a main controller connected to the laser generator, the laser controller, the thermal image generator and the lock-in processor and wherein the main controller controls operation of the laser generator and the thermal image generator to be synchronized with each other.

In an example embodiment, the periodic CW laser beam causes the plurality of chips to undergo periodic heating and cooling.

In an example embodiment, the thermal image generator comprises: a base plate between the laser unit and the wafer carrier and having a plurality of penetrating holes, at least two of the inspection laser beams penetrating each of the penetrating holes; and a plurality of thermal image chips arranged on a surface of the base plate and detecting thermal waves radiated from the plurality of chips, thereby generating the thermal images corresponding to the plurality of chips.

In an example embodiment, the thermal image generator comprises an infrared camera.

According to example embodiments of the present inventive concepts, the CW layer may be transformed into the inspection laser beam having a cross-sectional optical size smaller than the surface size of the semiconductor chip and a plurality of the semiconductor chips may be simultaneously and partially excited by the inspection laser beam. The thermal images may be generated from the scanning points of the chip surface and may be processed by the lock-in amplitude technology and the hold exponent technology, thereby forming the surface image in which the surface defect may be displayed accurately and clearly. Accordingly, the time and accuracy of the surface inspection process may be sufficiently improved. The holder exponent analysis and the noise filtering may allow the operator to visually inspect the surface defect on the chip surface.

Particularly, the time reduction of the surface inspection process may sufficiently improve an overall manufacturing efficiency of the semiconductor chips in case that much more semiconductor chips may be arranged on a large-diameter wafer.

BRIEF DESCRIPTION OF THE DRAWINGS

These and other features of the inventive concepts will become more apparent by describing in detail exemplary embodiments thereof with reference to the accompanying drawings of which.

DETAILED DESCRIPTION OF EMBODIMENTS

Figure 1:
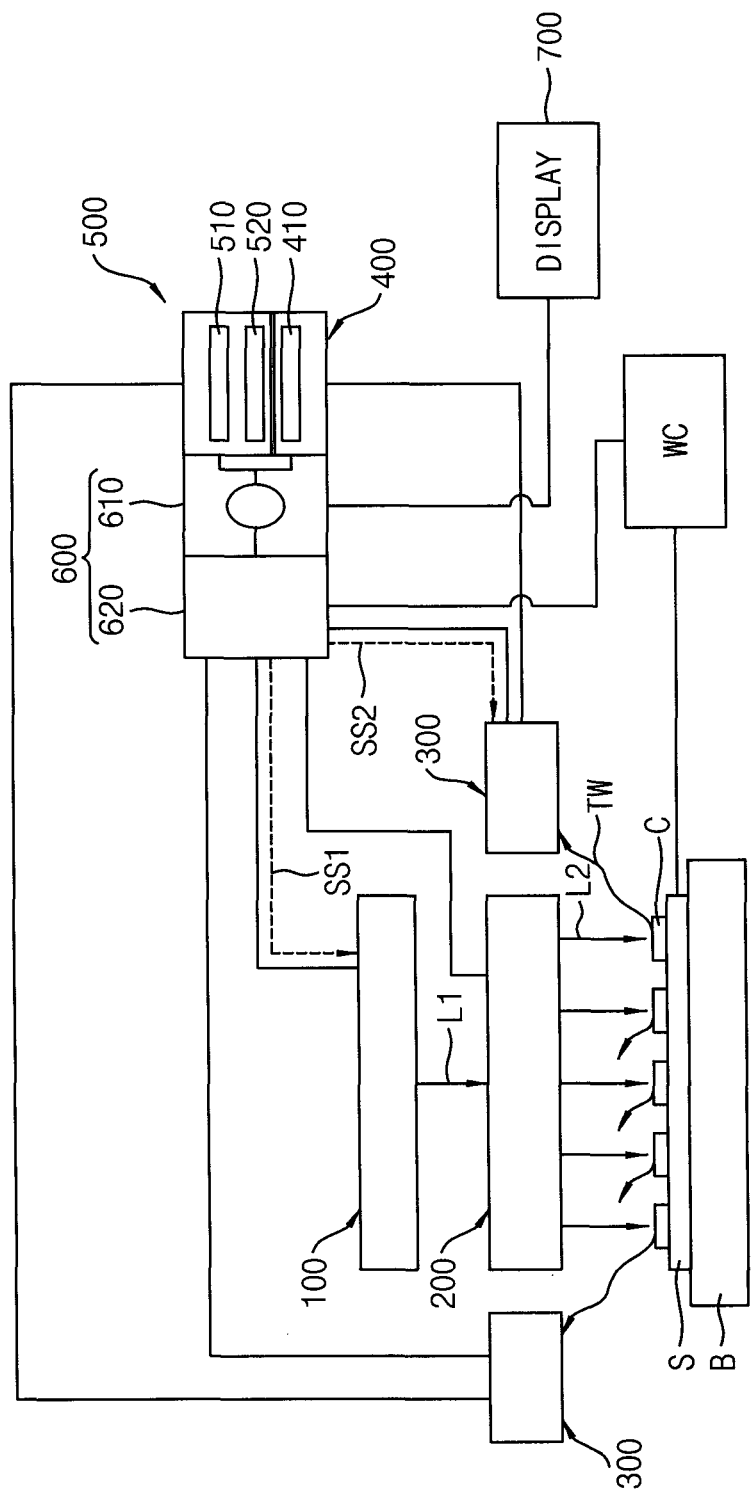
FIG. 1 is a structural view illustrating an apparatus for inspecting surfaces of semiconductor chips in accordance with an exemplary embodiment of the present inventive concepts.

Various example embodiments will be described more fully hereinafter with reference to the accompanying drawings, in which some example embodiments are shown. The present inventive concepts may, however, be embodied in many different forms and should not be construed as limited to the example embodiments set forth herein. Rather, these example embodiments are provided so that this disclosure will be thorough and complete, and will fully convey the scope of the present inventive concepts to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present inventive concepts.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of the present inventive concepts. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present inventive concepts.

Unless otherwise defined, all terms (including technical and scientific terms) used herein have the same meaning as commonly understood by one of ordinary skill in the art to which the inventive concepts belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, example embodiments will be explained in detail with reference to the accompanying drawings.

FIG. 1 is a structural view illustrating an apparatus for inspecting surfaces of semiconductor chips in accordance with an exemplary embodiment of the present inventive concepts.

Referring to FIG. 1, in some embodiments, the apparatus 1000 for inspecting surfaces of semiconductor chips (hereinafter, referred to as surface inspection apparatus) in accordance with an exemplary embodiment of the present inventive concepts may include a laser generator 100 generating a periodic continuous wave (CW) laser L1, a laser controller 200 transforming the periodic CW laser L1 into an inspection laser beam L2 of which a beam size is smaller than a surface size of the semiconductor chip C and irradiating the inspection laser beam L2 onto a plurality of the semiconductor chips C such that the semiconductor chips C are partially and, in some embodiments, simultaneously heated by the inspection laser beam L2, a thermal image generator 300 detecting thermal waves TW radiated from the semiconductor chips C in response to the inspection laser beam L2 and generating thermal images corresponding to the thermal waves, and a lock-in processor 400 processing the thermal image by using a lock-in thermography technique, thereby generating a lock-in thermography image of the thermal image in which a surface defect is included. The surface inspection apparatus 1000 may further include an image processor 500 processing the lock-in amplitude images, thereby generating a surface image of each of the semiconductor chips C by which the surface defect is visually inspected.

A main controller 600 may be connected to the laser generator 100, the laser controller 200, the thermal image generator 300 and the lock-in processor 400 and may control the laser generator 100 and the thermal image generator 300 to cause them to be synchronized with each other.

In an example embodiment, the laser generator 100 may generate a continuous laser L1 having a sufficiently low power for preventing damage to the semiconductor chips C. In this manner, the laser generator 100 generates a low-powered continuous wave (CW) laser. Particularly, the CW laser L1 may have a periodic waveform, thus the CW laser L1 may be periodically irradiated on the surface of the semiconductor chip C, as described in detail herein.

Figure 2:
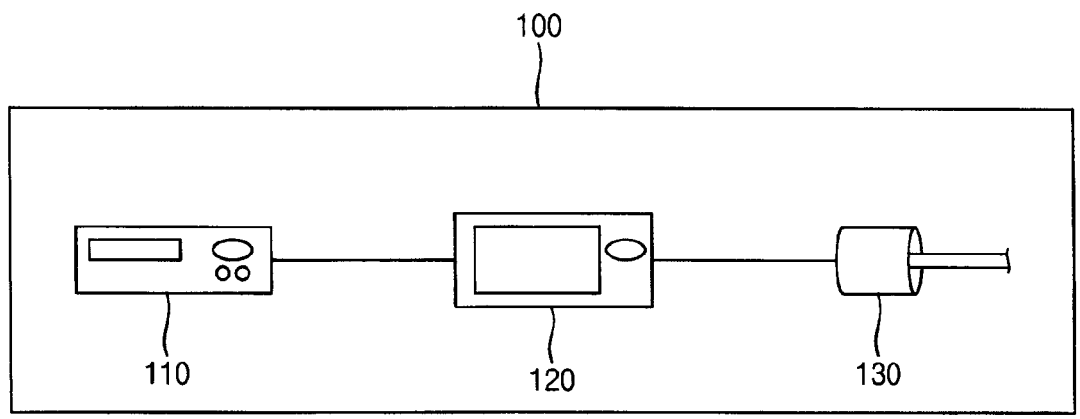
FIG. 2 is a structural view illustrating the laser generator shown in FIG. 1 in accordance with an example embodiment of the present inventive concepts.

FIG. 2 is a structural view illustrating the laser generator shown in FIG. 1 in accordance with an example embodiment of the present inventive concepts.

Referring to FIG. 2, the laser generator 100 may include a function generator 110 generating a periodic waveform voltage in response to a trigger signal, a modulating driver 120 amplifying the waveform voltage and converting the waveform voltage into a modulated current having a period of the periodic waveform voltage, and a laser oscillator 130 oscillated by the modulated current thereby emitting the periodic CW laser beam that is modulated in accordance with the modulated current.

For example, the function generator 110 may generate a voltage signal having a periodic waveform in response to a trigger signal that may be applied by the main controller as a start signal of the surface inspection process to the semiconductor chip C. The waveform of the voltage signal may function as a modulation base for modulating the CW laser in such a waveform that may be suitable for inspecting the chip surfaces.

In the present example embodiment, the function generator 110 may generate the voltage signal to have a periodic square waveform. Thus, the CW laser L1 may be modulated by the square waveform having the same period T as the voltage signal. The square waveform may include a section corresponding to an active mode in which the CW laser L1 may be caused to irradiate the chip surface and a section corresponding to an inactive mode in which the irradiation of the CW laser L1 of the chip surface may be interrupted. Thus, the semiconductor chip C may be repeatedly and periodically heated and periodically allowed to cool by application of the periodic square waveform CW laser L1.

In some embodiments, the modulating driver 120 may receive the periodic voltage signal from the function generator 110 and may amplify and modulate the voltage signal. Then, the modulated voltage signal may be converted into the modulated current signal in the modulating driver 120. For example, in some embodiments, the modulating driver 120 may include a laser diode driver (LDD).

The laser oscillator 130 may include a resonator (not shown) that may be activated by the modulated current signal and may continuously output a laser having a uniform intensity. Since the resonator may be periodically activated by the modulated current signal, the laser beam may also be output as a periodic waveform of the modulated current signal. Therefore, the laser oscillator 130 may generate the periodic CW laser L1 having the same period T as the modulated current signal. Since the periodic voltage signal may be generated into the square waveform and the CW laser L1 is modulated by the periodic square waveform, the semiconductor chips C that are subject to the output of the periodic CW laser L1 may undergo periodically repeated heating and cooling at each scanning point of the semiconductor chip C.

In an example embodiment, the laser controller 200 may geometrically transform the CW laser L1 into the inspection laser beam L2 in such a way that the inspection laser beam L2 may be irradiated to a plurality of the semiconductor chips C, particularly, to at least a surface portion of each semiconductor chip C. Therefore, a plurality of the semiconductor chips C may be partially and simultaneously heated at least at a scanning point to which the inspection laser beam L2 may be irradiated. Further, the thermal image generator 300 may detect a thermal wave radiated from each of the scanning points of each semiconductor chip and may generate the thermal image corresponding to each of the scanning points.

In some embodiments, the laser controller 200 may generate and irradiate the inspection laser beam L2 to each scanning point of the semiconductor chip C and the thermal image generator 300 may generate the thermal images from each scanning point, so that the configuration of the thermal image generator 300 may be varied in accordance with the configuration of the laser controller 200. For that reason, the laser controller 200 and the thermal image generator 300 may be described in detail together with each other herein.

Figure 3A:
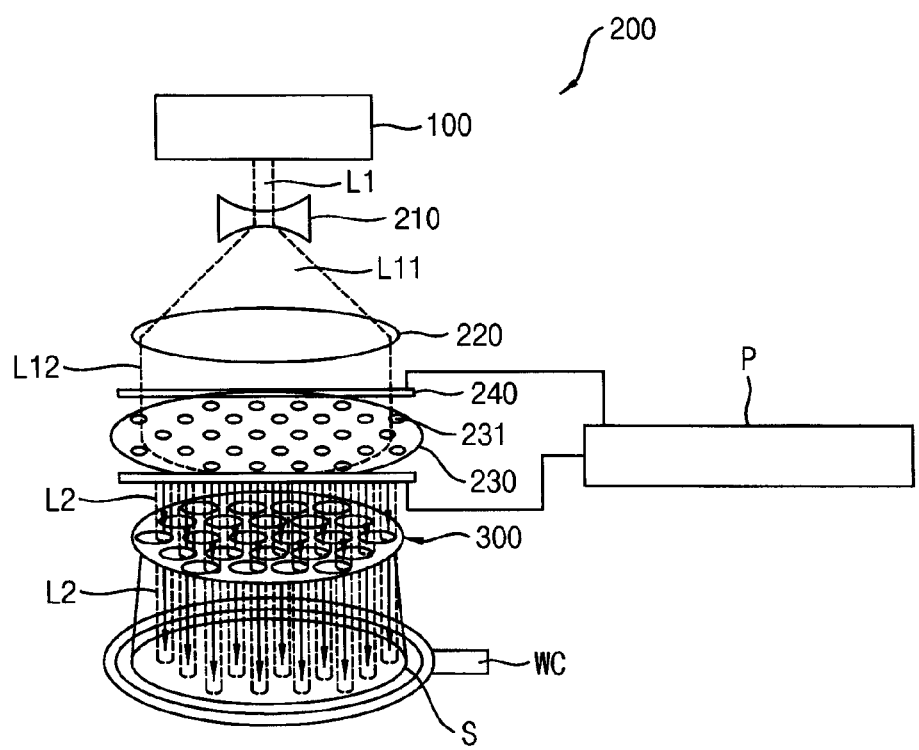
FIG. 3A is a view illustrating a combination of the laser controller and the thermal image generator of the apparatus shown in FIG. 1.

FIG. 3A is a view illustrating a combination of the laser controller and the thermal image generator of the apparatus shown in FIG. 1.

Referring to FIG. 3A, the laser controller 200 may include a beam expander 210 expanding a bundle of rays of the CW laser L1 thereby generating an expanded laser L11, a beam splitter 230 splitting the expanded laser L11 into a plurality of parallel spot beams as the inspection laser beam L2, and a position guide 240 configured to vary the relative position of the beam splitter 230 with respect to a substrate S on which a plurality of the semiconductor chips C may be arranged. Each of the parallel spot beams may have a cross-sectional beam size smaller than a surface of the semiconductor chip C and thus, in some embodiments, at least two parallel spot beams may be individually irradiated onto the surface of a single semiconductor chip C. The scanning points of the semiconductor chips C may be changed and altered by the position guide 240.

In some embodiments, the output of the CW laser L1 may have optical characteristics of a relatively small optical cross-sectional size and advanced directivity and may be configured into a single point beam, so that the CW laser L1 does not simultaneously irradiate a plurality of the semiconductor chips C. Thus, in this case, a bundle of the rays of the CW laser L1 may be expanded by the beam expander 210 for simultaneous irradiation to a plurality of the semiconductor chips C.

In the present example embodiment, the beam expander 210 may transform the shape of the CW laser L1 from the point beam to a surface beam. In some embodiments, two or more lenses (not shown) of which the focus points may coincide may be arranged in a line in the beam expander 210, so that the bundle of the rays of the CW laser L1 may be expanded according to the ratio of the focus distances of the lenses. As a result, the shape of the CW laser L1 may be transformed to the surface beam from the point beam, thereby generating the expanded laser L11 as the surface beam.

In the beam expander 210, the bundle of the rays of the CW laser L1 may be expanded in such a way that the rays may be distributed in accordance with a Gaussian distribution around the focus point of the lens in the beam expander 210. Thus, the expanded laser L11 may have non-uniform intensity across the optical cross-sectional surface of the surface beam. For that reason, a flat beam generator 220 may be further arranged between the beam expander 210 and the beam splitter 230. The flat beam generator 220 may convert a ray distribution of the expanded beam L11 from a Gaussian distribution into a uniform distribution, so that the expanded beam L11 may be converted to a flat beam L12 having a uniform intensity. Subsequently, the flat beam L12 may be split into the parallel spot beams having the uniform intensity by the beam splitter 230. For example, in some embodiments, the flat beam generator 220 may include a beam homogenizer that may include diffraction optical elements and optical lenses.

The beam splitter 230 may split the flat beam L12 into a plurality of parallel spot beams that may be irradiated onto the surface of the semiconductor chip C as the inspection laser beam L2. That is, the point beam of the CW laser L1 may be transformed into a plurality of the spot beams in parallel with one another through the beam expander 210, the flat beam generator 220 and the beam splitter 230. A plurality of the spot beams may be irradiated onto the substrate S on which a plurality of the semiconductor chips C may be arranged, so that the spot beams may function as the inspection laser beam L2. Accordingly, the inspection laser beam L2 may be simultaneously irradiated onto a plurality of the semiconductor chips C.

For example, the beam splitter 230 may include a plurality of beam passing holes 231 through which the parallel spot beams of the inspection laser beam L2 individually pass toward the substrate S in such a way that the cross-sectional beam size of the inspection laser beam L2 is controlled by a hole size of the beam passing hole 231. In the present example embodiment, the beam splitter 230 may include a pattern mask having the beam passing holes 231 and comprising photoresist materials.

Some of the flat beam L12 may selectively pass through the pattern mask via the beam passing holes 231, thereby transforming into the spot beams, while the remainder of the flat beam L12 may be blocked by the pattern mask. Thus, the flat beam L12 may be split into a plurality of spot beams in parallel with one another in accordance with the arrangement of the beam passing holes 231. Therefore, a plurality of the parallel spot beams may be irradiated onto the substrate S and a plurality of the semiconductor chips C may be irradiated by the parallel spot beams.

A cross-sectional size of the spot beam may be varied according to the size of the beam passing hole 231. In the present example embodiment, the beam passing hole 231 may be prepared to have the size smaller than a surface size of the semiconductor chip C, so that the spot beam may be split to have the cross-sectional size smaller than the surface size of the chip C. Therefore, a plurality of spot beams may be irradiated onto the surface of a single chip C. That is, each of the semiconductor chips C may have a plurality of scanning points on a surface, and the inspection laser beam L2 may be individually irradiated onto the scanning points. As a result, each of the scanning points may function as an independent heat source from which the thermal wave may be radiated in an outwardly oriented direction.

Accordingly, the beam passing holes 231 may correspond to the scanning points on the chip C in a one-to-one relationship and the number of the beam passing holes 231 may be several times the number of semiconductor chips C on the substrate S. For example, in a case where three hundred (300) semiconductor chips C may be arranged on the substrate S and three (3) scanning points may be allotted to each chip, 900 beam passing holes 231 may be prepared with the beam splitter 230. In the present example embodiment, the number of the beam passing holes 231 may be three to five times of the number of the semiconductor chips C, so that three to five spot beams may be individually irradiated onto a single semiconductor chip C.

The position guide 240 may guide the beam splitter 230 and may change a relative position of the beam splitter 230 with respect to the substrate S, so that the scanning point of the semiconductor chip C may be shifted by the movement of the position guide 240. For example, the beam splitter 230 may be shaped into the substrate S and the position guide 240 may include a pair of linear guides each of which may make contact with an edge side of the beam splitter 230.

In some embodiments, the movement of the position guide 240 may be controlled by a position controller P that may be activated by the main controller 600. Therefore, the relative position of the substrate S and the beam splitter 230 may be adjusted by the main controller 600 in such a way that the inspection laser beam L2 may be accurately irradiated onto the expected scanning points of the semiconductor chips C.

The thermal waves TW may be radiated from each of the scanning points of each semiconductor chip C in response to each spot beam and may be detected by the thermal image generator 300.

For example, the thermal image generator 300 may include a base plate 310 interposed between the beam splitter 230 and the substrate S and having a plurality of penetrating holes 311, and a plurality of thermal image chips 320 arranged on a surface of the base plate 310 and detecting the thermal waves TW radiated from the scanning points of the semiconductor chips C, thereby generating the thermal images at each of the scanning points by a unit of the semiconductor chip C. In the present example embodiment, at least two parallel spot beams may penetrate through each of the penetrating holes 311 of the base plate 310.

Figure 3B:
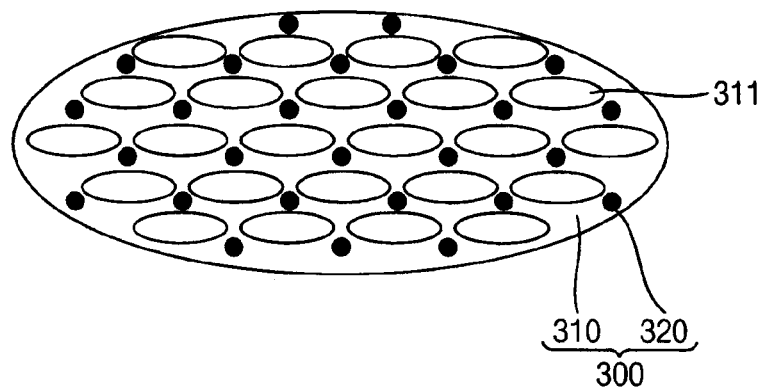
FIG. 3B is a structural view illustrating the thermal image generator shown in FIG. 3A.

FIG. 3B is a structural view illustrating the thermal image generator shown in FIG. 3A.

As illustrated in FIG. 3B, in some embodiments, the base plate 310 may be shaped into a circular disc having a shape and size similar to the substrate S and the penetrating holes 311 may be distributed uniformly on the entire surface of the base plate 310.

The penetrating hole 311 may have a sufficient size through which a group of the spot beams functioning as the inspection laser beam L2 may pass, so that several semiconductor chips C may be exposed through a single penetrating hole 311. In such a case, the thermal image chip 320 may be positioned on a rear surface of the base plate adjacent to each penetrating hole 311, so that thermal image chip 320 may detect the thermal waves TW that may be radiated from the group of the semiconductor chips C exposed to the penetrating hole 311.

In the present example embodiment, six to seven chips C may be exposed by the incident radiation through the single penetrating hole 311 and thus the thermal image chip 320 may detect the thermal waves TW radiated from each scanning point of six to seven chips C.

In an example where three scanning points may be set on the surface of the semiconductor chip C, 18 to 21 spot beams may pass through the penetrating hole 311 and the thermal image chip 320 may detect the thermal waves TW from 18-21 scanning points of the chips C. Thus, the thermal images may be generated at each of the scanning points and may be stored by a unit of the chip C. That is, three thermal images generated from the three scanning points of the same chip C may be stored as the same group of the thermal images.

Particularly, the thermal wave may include an infrared wave propagating from the scanning point of the chip C with a Gaussian distribution and the thermal image chip 320 may include an infrared detection chip for detecting the infrared waves. Otherwise, the thermal image generator 300 may include an infrared camera in place of the thermal image chip 320.

Figure 4:
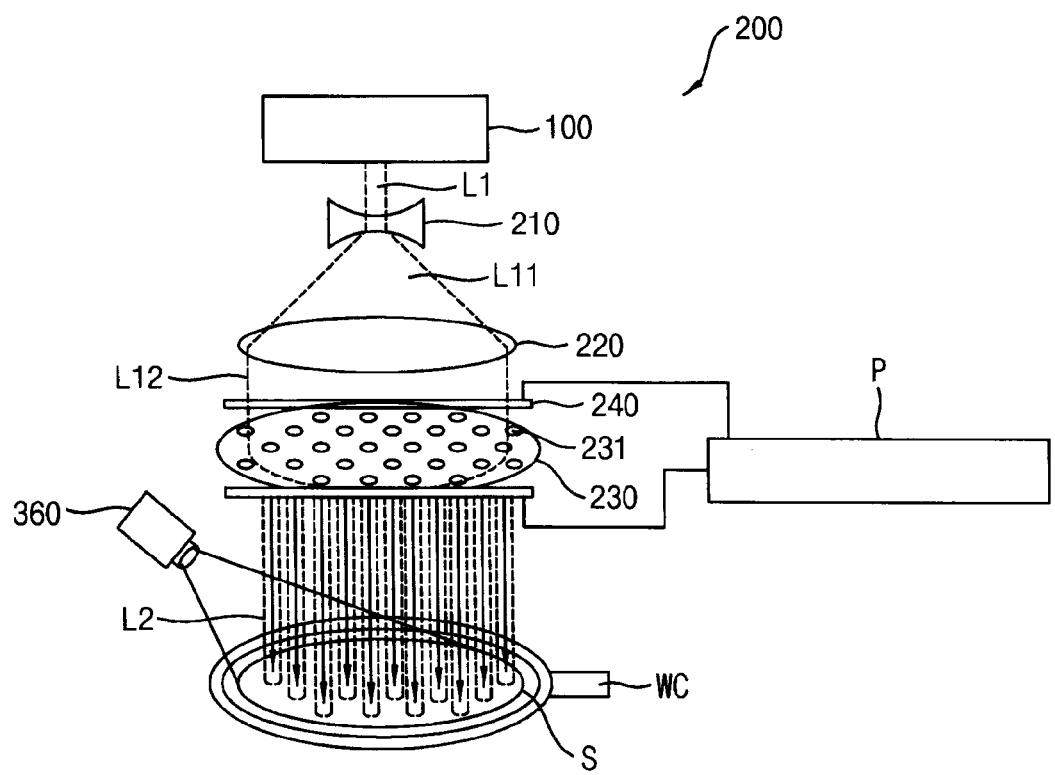
FIG. 4 is a view illustrating another combination of the laser controller and the thermal image generator of the apparatus shown in FIG. 1.

FIG. 4 is a view illustrating another combination of the laser controller and the thermal image generator of the apparatus shown in FIG. 1. The combination of the laser controller and the thermal image generator in FIG. 4 has substantially the same structure and configuration as the combination shown in FIG. 3A, except that the thermal image chip 320 may be replaced by the infrared camera 360. Thus, in FIG. 4, the same reference numerals denote the same elements in FIG. 3A, and any further detailed descriptions on the same elements will be omitted hereinafter.

As shown in FIG. 4, the thermal image generator 300 may include an infrared camera system 360 in place of the thermal image chip 320.

The infrared camera system 360 may detect the thermal waves TW radiated from the scanning points of the chips C and may generate the thermal images corresponding to each of the scanning points. Then, the thermal images corresponding to the same chip C may be stored into the same group of the thermal images. A layout of the semiconductor chips C on the substrate S may be transferred to the infrared camera system 360 and the scanning points may be classified by a unit of the chip C based on the layout. Thus, the thermal images corresponding to each scanning point may be stored by a unit of the chip C.

A camera of the infrared camera system 360 may be located at various positions as long as the inspection laser beam L2 may not be interrupted and the resolution of the thermal image may be sufficient for inspecting surface defects of the chip C. For example, the camera of the infrared camera system 360 may be positioned over the substrate S at a slightly slanted position relative to the path of the inspection laser beam L2.

The substrate S may be loaded onto an inspection board B by a wafer carrier WC such as a wafer cassette and the laser controller 200 and the thermal image generator 300 may be located at a suitable position with respect to the substrate S by the main controller 600.

In a modified example embodiment, the laser controller 200 may be located at a slanted or angled position relative to the substrate S and the camera of the infrared camera system 360 may be located at a position that is substantially perpendicular to the substrate S, thereby improving the image quality such as the resolution of the thermal images.

The thermal generator 300 may detect the thermal waves TW from each scanning point for a predetermined time and may generate the thermal images corresponding to the scanning point in a time domain.

Figure 5A:
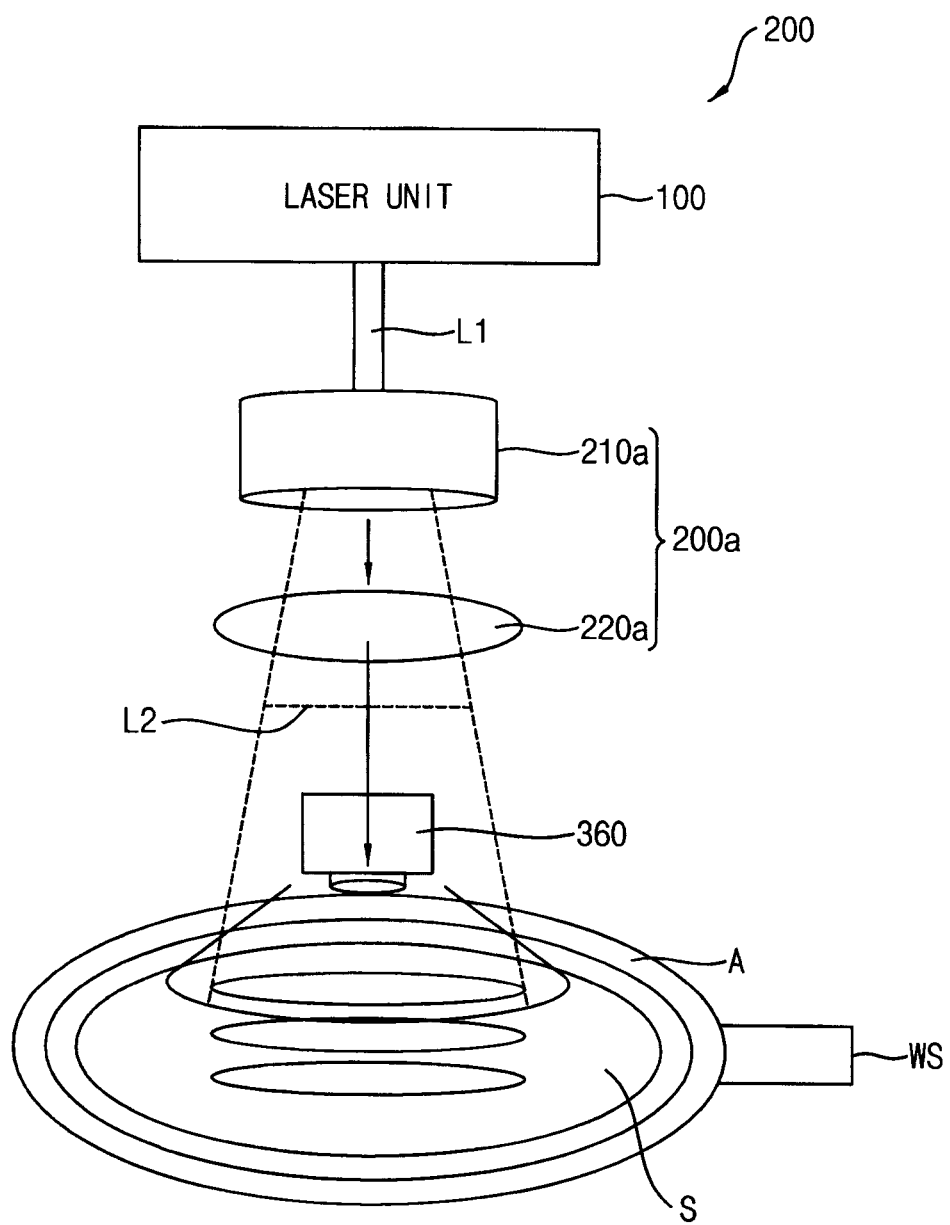
FIG. 5A is a view illustrating still another combination of the laser controller and the thermal image generator of the apparatus shown in FIG. 1.

FIG. 5A is a view illustrating still another configuration of the laser controller and the thermal image generator of the apparatus shown in FIG. 1. The combination of the laser controller and the thermal image generator in FIG. 5A has substantially the same structure and configuration as the combination shown in FIG. 4, except for the laser controller.

Thus, in FIG. 5A, the same reference numerals denote the same elements in FIG. 4, and any further detailed descriptions on the same elements will be omitted hereinafter.

Referring to FIG. 5A, a modified laser controller 200a may include a line beam generator 210a transforming the CW laser L1 into a linear beam as the inspection laser beam L2 in such a shape that the linear beam may extend along a first direction x of the substrate S and may have a beam width smaller than the surface size of the semiconductor chip C, and a beam provider 220a providing the linear beam to a plurality of semiconductor chips C arranged in the first direction x in such a way that the linear beam may be simultaneously irradiated onto a plurality of scanning points of each semiconductor chip C along the first direction x.

For example, the line beam generator 210a may include a plurality of slant mirrors between an inlet portion and an exit portion thereof, so that the point beam of the CW laser L1 may be transformed into the line beam extending along the first direction x.

Particularly, since the beam width Wb of the linear beam may be smaller than a chip length Lc of the semiconductor chip C, the linear beam may be irradiated onto a portion of the semiconductor chip C. Thus, the inspection laser beam L2 may be simultaneously irradiated onto a plurality of scanning points of each of the semiconductor chips along the first direction x.

The beam provider 220a may provide the linear beam to a plurality of the scanning points of each semiconductor chip C along the first direction x. For example, in some embodiments, the beam provider 220a may include a Galbano mirror interposed between the substrate S and the line beam generator 210a.

Figure 5B:
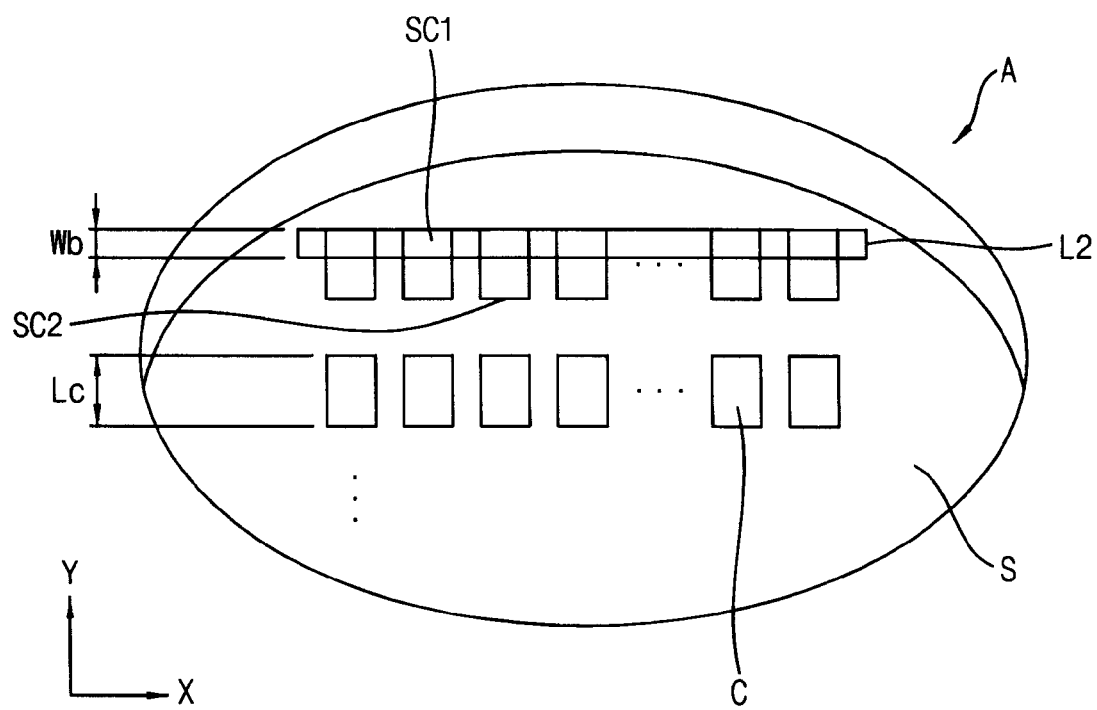
FIG. 5B is an enlarged view illustrating a portion A of FIG. 5A.

FIG. 5B is an enlarged view illustrating a portion A of FIG. 5A.

As illustrated in FIG. 5B, the optical characteristics of the line beam generator 210a may be controlled in such a way that the CW laser L1 may be transformed into the inspection laser beam L2 of which the beam width Wb may be smaller than the chip length Lc of the semiconductor chip C on the substrate S.

In some embodiments, the inspection laser beam L2 may be controlled to be irradiated to the scanning points by the beam provider 220a. For example, a plurality of first scanning points sc1 of the semiconductor chips C which may be arranged in the first direction x (first scanning line) may be simultaneously excited by the inspection laser beam L2. Then the path of the inspection laser beam L2 may be changed by the beam provider 220a, and a plurality of second scanning points sc2 of the same semiconductor chips C which may be arranged in the first direction x (second scanning line) may be simultaneously excited by the inspection laser beam L2. Thus, the semiconductor chips C arranged in the first direction x may be excited or heated by the subsequent double scanning of the inspection laser beam L2, and the thermal images may be generated from each of the scanning points sc1 and sc2.

While the present example embodiment discloses that a pair of the scanning points may be directed toward a single semiconductor chip C, in some embodiments, three or more scanning points can optionally be prepared at a single chip C for improving the quality of the thermal images.

In some embodiments, the thermal waves TW may include infrared waves propagating from each of the scanning points sc1 and sc2 with a Gaussian distribution and the thermal image generator includes an infrared camera system detecting the infrared waves and generating the thermal images corresponding to the infrared waves at each of the scanning points sc1 and sc2 by a unit of the semiconductor chip C. The infrared camera system may have substantially the same structures and configurations as described with reference to FIG. 4; thus, any detailed descriptions on the infrared camera system will be omitted.

Referring again to FIG. 1, the thermal images generated by the thermal image generator 300 may be processed by image processing algorithms, thereby generating the surface image of the chip C in which the surface defects may be visually displayed. In the present example, the thermal image is converted into the lock-in amplitude images by a lock-in thermography technique. Further, in some embodiments, the lock-in amplitude images may be processed by a hold exponent analysis for generating the surface image of the chip C.

For example, the lock-in processor 400 includes a lock-in amplitude processor 410 processing amplitudes of the thermal waves TW to thereby remove dummy images corresponding to dummy waves caused by thermal disturbances from the thermal images. Thus, lock-in amplitude images may be generated by the lock-in processor 400 corresponding to the thermal images for each scanning point as the lock-in thermography images.

The thermal images, which may be generated at each scanning point of the semiconductor chips C in the time domain, may be transferred to the lock-in amplitude processor 410.

The lock-in amplitude processor 410 may select an arbitrary region of the thermal images in a region of interest that may be suspected to indicate a surface defect. Lock-in amplitude values may be individually calculated for every pixel of the interest region by using lock-in amplitude algorithms, which may be configured into the lock-in amplitude processor 410, and all of the lock-in amplitude values of the interest region may be assembled. The lock-in amplitude image may be generated from the assembled lock-in amplitude values in a time domain.

The inspection laser beam L2 may be repeatedly operated in the active mode and the inactive mode in a time period T, and thus the semiconductor chip C may be repeatedly heated and cooled in accordance with the active mode and the inactive mode. Thus, any temperature gradients of the surface of the chip C may be primarily caused by the repeated heating and cooling of the chip C and the thermal waves TW detected from the scanning points may be primarily caused by the temperature gradient of the chip surface. However, any additional thermal disturbances such as such as environmental temperature and dummy thermal waves TW reflected from the infrared camera may also have an effect on the detected thermal waves, and thus the thermal images may inadvertently include dummy images caused by the thermal disturbances. The lock-in amplitude algorithms may be configured to remove the dummy images from the thermal images and thus the lock-in amplitude images may be configured to reflect only the temperature gradient of the chip surface caused by the repeated heating and cooling due to the inspection laser beam L2.

The image processor 500 may process the lock-in amplitude images by using various image process technologies, thereby generating the surface image of each of the semiconductor chips by which the surface defect is visually displayed.

For example, the image processor 500 may include a discontinuous image detector 510 that processes the lock-in amplitude image and detecting image singularities from the lock-in amplitude image to thereby generate a visually enhanced lock-in amplitude image in which discontinuous portions are visually shown on the lock-in amplitude image, and a noise filter 520 removing noises from the visually enhanced lock-in amplitude image, thereby generating the surface image of the semiconductor chip C.

In some embodiments, the thermal waves TW may propagate from the scanning point with a Gaussian distribution. When the thermal waves TW may meet a surface defect such as a crack or scratch, the propagation of the thermal waves TW may be interrupted and thus the thermal signature may not be detected from the position where the surface defect exists. Therefore, the thermal waves TW may be deformed or distorted at the defect position on the chip surface. Since the thermal images may be generated from the thermal waves, the thermal images may also be deformed or no thermal images may be generated at the defect position of the chip surface. The thermal image or the lock-in amplitude image may be discontinuous or have a singularity point at the defect position. That is, the lock-in amplitude images may include image singularity or discontinuous area corresponding to the defect position of the chip surface.

In the present example embodiment, the discontinuous image detector 510 may include a holder exponent analyzer (not shown) in which the image singularities are detected through a holder exponent analysis process. Thus, the discontinuous portion or the image singularities may be clearly displayed in the lock-in amplitude image, and the discontinuous image detector 510 may generate a visually enhanced lock-in amplitude image. As a result, the operator may visually inspect the surface defect much more accurately and easily.

The noise filter 520 may remove various noise elements from the visually enhanced lock-in amplitude image and thus the surface defect may be much more clearly displayed in the surface image.

In the present example embodiment, the noise filter 520 may include a statistical analyzer (not shown) in which pixel values of each pixel of the visually enhanced lock-in amplitude image may be analyzed and may be statistically processed for improving the clarity of the surface defect. For example, the statistical analyzer may generate a Weibull distribution of the pixel values of the visually enhanced lock-in amplitude image and then some of the pixel values within a specific confidence interval just display the visually enhanced lock-in amplitude image, thereby forming the surface image in which the surface defect is more clearly displayed. In some embodiments, the pixel value corresponding to the selected confidence interval may be set as a threshold value, and the pixel values over the threshold value may be just displayed in the visually enhanced lock-in amplitude image, which may be formed into the surface image.

Accordingly, the dummy images caused by the thermal disturbances may be removed from the thermal images and surface defect may be more clearly displayed in the surface image while suppressing or eliminating noise. Therefore, the surface defect of the semiconductor chip C may be more accurately detected by the surface inspector 1000 in a shorter inspection time.

The main controller 600 may include a signal unit 610 constructed and arranged to detect an initiating signal and to generate various control signals to be provided to the surface inspection apparatus 1000 and a transfer unit 620 driven by the signal unit 610 and transferring the control signals to the laser generator 100, the laser controller 200, the thermal image generator 300, the lock-in processor 400 and the image processor 500.

Further, a display terminal 700 may be provided for displaying the surface image. The display terminal 700 may be connected to the transfer unit 620 of the main controller 600 and the surface image generated from the image processor 500 may be displayed on the display terminal 700.

Particularly, the transfer unit 620 of the main controller 600 may control the laser generator 100 and the thermal image generator 300 so that they are synchronized with each other. Thus, a first control signal SS1 for generating the CW laser L1 and a second control signal SS2 for generating the thermal images may be synchronized with each other. Therefore, the CW laser L1 may match with the thermal images by every period T thereof. In the present example embodiment, the synchronization signal for synchronizing the first and the second control signals may be transferred together with the trigger signals that may be simultaneously applied to the laser generator 100 and the thermal image generator 30.

Thus, the CW laser L1 may be repeatedly generated at the period T and the resulting thermal images may also be generated to correspond with the CW laser L1. That is, the thermal images may be generated by the corresponding CW laser L1 operating at the period T.

According to the example embodiments of the surface inspection apparatus, the CW laser output beam may be transformed into the inspection laser beam having the cross-sectional optical size smaller than the surface size of the semiconductor chip. In particular, a plurality of semiconductor chips may be simultaneously and partially excited by the inspection laser beam. The thermal images may be generated from every scanning point of the chip surface and may be processed by the lock-in amplitude technology and the hold exponent technology, thereby forming the surface image in which the surface defect may be accurately and clearly displayed.

Hereinafter, a method of inspecting surfaces of semiconductor chips will be described in detail by using the above surface inspection apparatus.

Figure 6:
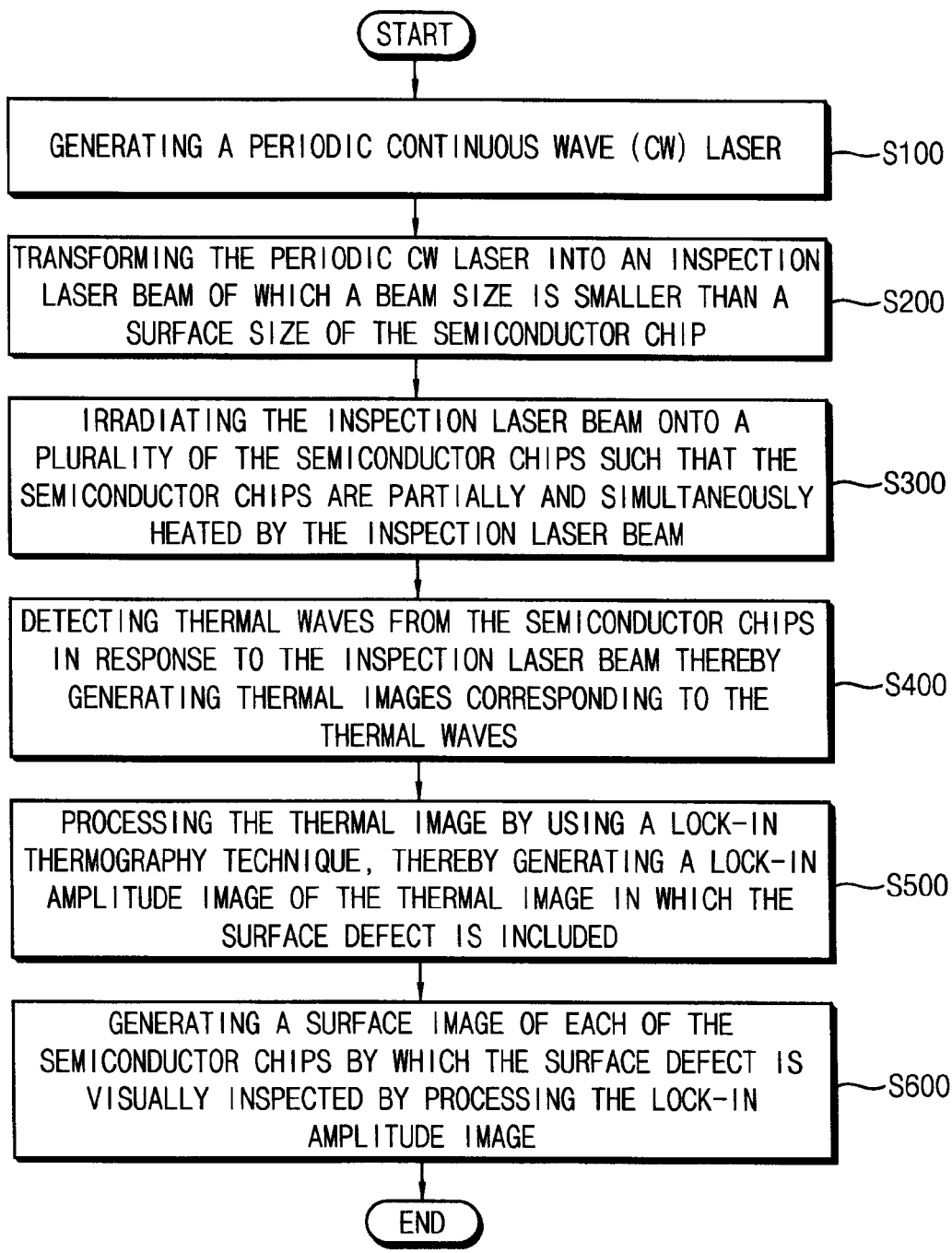
FIG. 6 is a flow chart showing a method of inspecting surfaces of semiconductor chips by using the surface inspection apparatus shown in FIG. 1.

FIG. 6 is a flow chart illustrating a method of inspecting surfaces of semiconductor chips by using the surface inspection apparatus shown in FIG. 1.

Referring to FIGS. 1 and 6, the periodic CW laser L1 may be generated in the laser generator 100 (step S100).

A trigger signal may be applied to the laser generator 100 by the main controller 600, and a periodic voltage signal may be generated from the function generator 110 by the first control signal SS1. The periodic voltage signal may be amplified and modulated in the modulating driver 120, thereby generating the modulated current signal. Then, the laser oscillator 130 may be driven by the modulated current signal, thereby generating the periodic CW laser L1.

The periodic CW laser L1 may be transformed into an inspection laser beam L2 of which the beam size may be smaller than the surface size of the semiconductor chip C (step S200).

For example, the point beam of the CW laser beam L1 may be split into a plurality of spot beams by the pattern mask of the laser controller 200 in such a way that the cross-sectional optical size of the spot beam may be smaller than the surface size of the chip C. Thus, a plurality of the spot beams may be irradiated onto a plurality of the semiconductor chips C as the inspection laser beam. That is, at least two parallel spot beams may be irradiated onto the chip surface of the semiconductor chip on the condition that the parallel spot beams may be simultaneously irradiated to a plurality of the semiconductor chips C on a single substrate S.

In another embodiment, the point beam of the CW laser L1 may be transformed into a linear beam extending along the first direction x of a substrate S on which a plurality of the semiconductor chips C may be arranged and having a beam width Wb smaller than the chip length Lc of the semiconductor chip C. That is, the CW laser L1 may be transformed into the linear beam as the inspection laser beam. The linear beam may be simultaneously irradiated onto a plurality of scanning points of each semiconductor chip along the first direction x.

The inspection laser beam L2 may be irradiated onto a plurality of the semiconductor chips C such that the surfaces of the semiconductor chips are partially and simultaneously heated by the inspection laser beam L2 (step S300).

In a case where the inspection laser beam L2 may include the parallel spot beams, a plurality of the spot beams may be simultaneously irradiated onto the chip surface of the semiconductor chip C since the cross-sectional optical size of the spot beam may be smaller than the surface size of the chip. Thus, multiple ones of the semiconductor chips C may be locally and partially heated or excited by the spot beams.

In a case where the inspection laser beam L2 may include the linear beam, the linear beam may be simultaneously irradiated onto a plurality of the semiconductor chips C along the first direction x of the substrate S. Since the beam width Wb of the linear beam may be smaller than the chip length Lc of the semiconductor chip C, the semiconductor chips C may be partially heated by the linear beam.

Then, as a result of the irradiation of the chips C, the thermal waves TW may be detected from the scanning points of the semiconductor chips C in response to the inspection laser beam L2 thereby generating the thermal images corresponding to the thermal waves TW (step S400).

For example, the infrared waves may be radiated from each scanning point of the chip C with a Gaussian distribution and the thermal image chip 320 or the infrared camera system 360 may detect the infrared waves. Then, the thermal images may be generated from the detected infrared waves at every scanning point of the chip C. The thermal images may be stored in the thermal image generator 300 by a unit of the chip C.

Figure 7A:
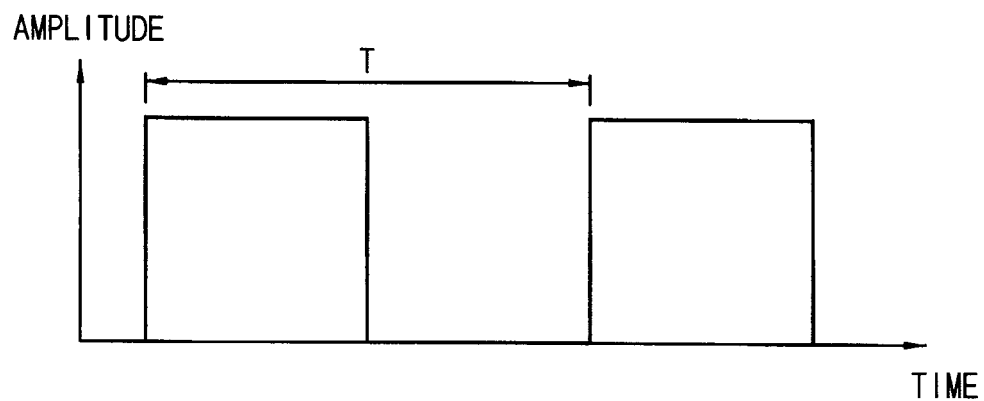
FIG. 7A is a graph showing the periodic CW laser generated from the laser generator.
Figure 7B:
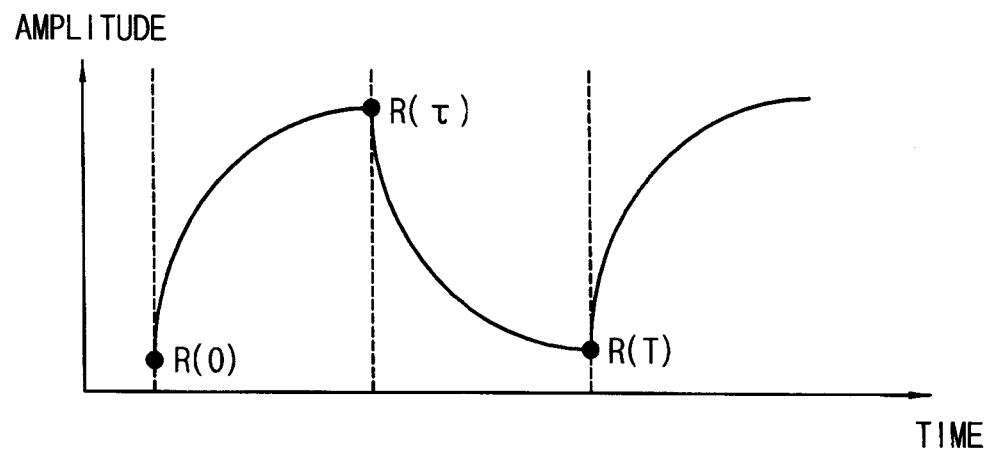
FIG. 7B is a graph showing the thermal wave detected from the scanning point in response to the CW laser.

FIG. 7A is a graph showing the periodic CW laser generated from the laser generator and FIG. 7B is a graph showing the thermal wave detected from the scanning point in response to the CW laser.

Referring to FIG. 7A, the CW laser L1 may be generated in a square waveform having a period T, so that the CW laser may be operated in an active mode for an active time T/2 and in an inactive mode for an inactive time T/2. In the active mode, the CW laser L1 may be generated at a uniform intensity I. Thus, the semiconductor chip C may be heated by the CW laser L1 having the uniform intensity I for the active time T/2 and may be cooled for the inactive time T/2.

As a result, as shown in FIG. 7B, the amplitude of the thermal wave may gradually increase for the active time, and finally may reach the peak point at time of T/2. Thereafter, the amplitude of the thermal wave may gradually decrease for the inactive time. The increase and decrease of the amplitude of the thermal wave may be repeated with the same period T as the CW laser may be repeatedly generated. That is, the generation of the CW laser L1 may be synchronized with the generation of the thermal image.

In some cases, the thermal images may include various dummy images caused by various thermal disturbances such as the emissivity of the chip surface and the reflective thermal waves TW from the infrared camera system 360. Thus, the resulting thermal image may be insufficient for inspecting the surface defects of the semiconductor chip C.

Thus, returning to FIG. 6, the thermal images may be processed by a lock-in thermography technique, thereby generating a lock-in amplitude image of the thermal image in which a surface defect is included (step S500).

The thermal image may cover an image area corresponding to the Gaussian distribution of the thermal wave. Thus, the lock-in amplitude processor 410 may select an area of the thermal images as the interest region which may be suspected to indicate the surface defect. Then, the lock-in amplitude values may be individually calculated for every pixel of the interest region by using lock-in amplitude algorithms, and the lock-in amplitude values of the interest region may be assembled. The lock-in amplitude image may be generated from the assembled lock-in amplitude values in the time domain.

The thermal images may include various dummy images caused by various thermal disturbances. However, the lock-in amplitude image may be locked with the temperature gradient just merely caused in response to the inspection laser beam L2, so that the dummy images caused by the thermal disturbances may be removed from the thermal images.

When a surface defect has a sufficiently large size, the large surface defect may be detected just by a single lock-in amplitude image. In contrast, when the surface defect has a relatively small size, the small surface defect may be accurately detected by comparison of the lock-in amplitude images that may be generated at different scanning points of the same semiconductor chip C. Since the beam size of the inspection laser beam L2 may be smaller than the surface size of the chip, several lock-in amplitude images may be generated from the same chip surface. Thus, the surface defects may be much more accurately detected by the comparison of the lock-in amplitude images for the same chip surface.

An additional image process may be performed on the lock-in amplitude image for even further retailed detection of the surface defect of the chip surface.

For example, the lock-in amplitude image may be further processed by the image processor 500, thereby generating a surface image visually displaying the surface defect (step S600). Therefore, the surface defect may be clearly shown on the surface image, which may increase the inspection efficiency and accuracy.

Figure 8:
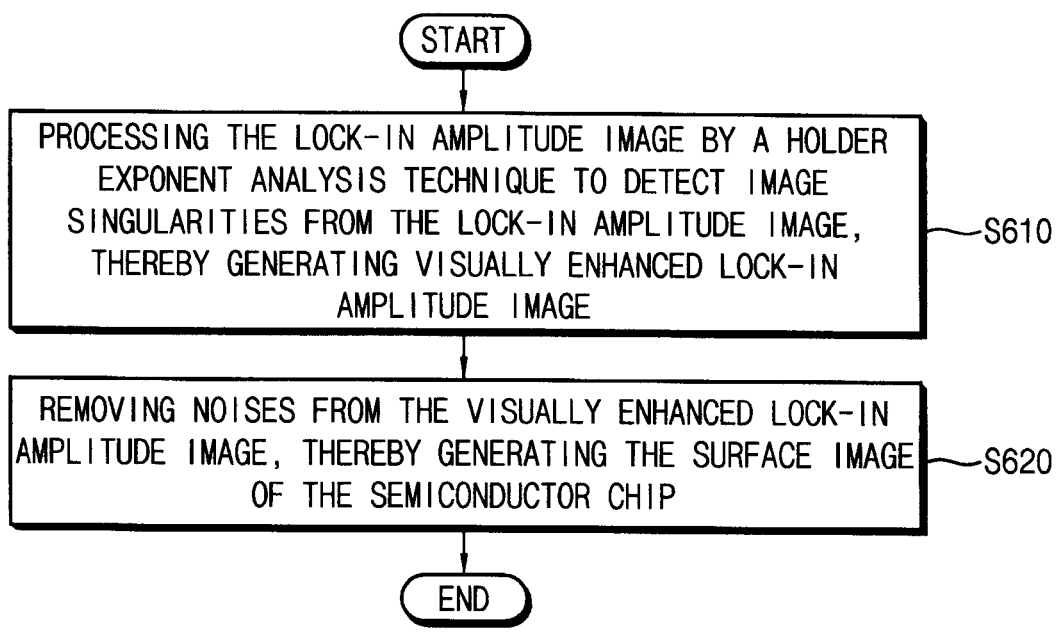
FIG. 8 is a flow chart showing the processing steps for a method of generating the surface image shown in FIG. 6.

FIG. 8 is a flow chart showing the processing steps for a method of generating the surface image shown in FIG. 6.

Referring to FIG. 8, in some embodiments, the lock-in amplitude image may be processed by a holder exponent analysis technique to detect the image singularities from the lock-in amplitude image, thereby generating visually enhanced lock-in amplitude image in which discontinuous portions are visually shown on the lock-in amplitude image (step S610).

The thermal waves TW may propagate from the scanning point with a Gaussian distribution. When the thermal waves TW meet the surface defect such as a crack and a scratch, the propagation of the thermal waves TW may be interrupted and thus the thermal image may not be detected from the position where the surface defect exists. Therefore, the thermal waves TW may be deformed or distorted at the defect position on the chip surface. Since the thermal images may be generated from the thermal waves, the thermal images may also be deformed or no thermal images may be generated at the defect position of the chip surface. Thus, the lock-in amplitude image may be discontinuous or may have singularity point at the defect position. That is, the lock-in amplitude images may include image singularity or a discontinuous area corresponding to the defect position of the chip surface.

The holder exponent analyzer in the discontinuous image detector 510 may detect the image singularities through a holder exponent analysis process. Thus, the discontinuous portion or the image singularities may be clearly displayed in the lock-in amplitude image, thereby generating the visually enhanced lock-in amplitude image. The operator may visually inspect the surface defect much more accurately and easily. Accordingly, the size, position and shape of the surface defect may be accurately detected by the surface image.

Thereafter, various forms of noise may be removed from the visually enhanced lock-in amplitude image, thereby generating the surface image of the semiconductor chip C (step S620).

For example, the pixel values of the visually enhanced lock-in amplitude image may be analyzed and statistically processed for improving the clarity of the surface defect. The statistical analyzer in the noise filter 520 may generate a Weibull distribution of the pixel values of the visually enhanced lock-in amplitude image and then some of the pixel values within a specific confidence interval just display the visually enhanced lock-in amplitude image, thereby forming the surface image in which the surface defect is clearly displayed. The pixel value corresponding to the selected confidence interval may be set as a threshold value, and the pixel values over the threshold value may be displayed in the visually enhanced lock-in amplitude image, which may be formed into the surface image.

According to the above exemplarily embodiments of the present inventive concepts, the CW laser output may be transformed into the inspection laser beam having a cross-sectional optical size that is smaller than the surface size of the semiconductor chip and a plurality of the semiconductor chips may be simultaneously and partially excited by the inspection laser beam. The thermal images may be generated from every scanning point of the chip surface and may be processed by the lock-in amplitude technology and the hold exponent technology, thereby forming the surface image in which the surface defect may be accurately and clearly displayed. Accordingly, the time and accuracy of the surface inspection process may be sufficiently improved. The holder exponent analysis and the noise filtering may allow the operator to visually inspect the surface defect on the chip surface.

Particularly, the time reduction of the surface inspection process may sufficiently improve an overall manufacturing efficiency of the semiconductor chips in a case where multiple semiconductor chips are arranged on a large-diameter wafer.

The foregoing is illustrative of example embodiments and is not to be construed as limiting thereof. Although a few example embodiments have been described, those skilled in the art will readily appreciate that many modifications are possible in the example embodiments without materially departing from the novel teachings and advantages of the present inventive concepts. Accordingly, all such modifications are intended to be included within the scope of the present inventive concepts as defined in the claims. In the claims, means-plus-function clauses are intended to cover the structures described herein as performing the recited function and not only structural equivalents but also equivalent structures. Therefore, it is to be understood that the foregoing is illustrative of various example embodiments and is not to be construed as limited to the specific example embodiments disclosed, and that modifications to the disclosed example embodiments, as well as other example embodiments, are intended to be included within the scope of the appended claims.

What is claimed is:

1. An apparatus for inspecting surfaces of semiconductor chips, comprising:
   a laser generator generating a periodic continuous wave (CW) laser;
   a laser controller transforming the periodic CW laser into an inspection laser beam of which a beam size is smaller than a surface size of the semiconductor chip and irradiating the inspection laser beam onto a plurality of the semiconductor chips such that the semiconductor chips are partially and simultaneously heated by the inspection laser beam;
   a thermal image generator detecting thermal waves radiated from the semiconductor chips in response to the inspection laser beam and generating thermal images corresponding to the thermal waves; and
   a lock-in processor processing the thermal image using a lock-in thermography technique, thereby generating a lock-in thermography image of the thermal image in which a surface defect is included,
   wherein the lock-in processor includes a lock-in amplitude processor processing amplitudes of the thermal waves to remove dummy images corresponding to dummy waves caused by thermal disturbances from the thermal images, thereby generating lock-in amplitude images corresponding to the thermal images for each scanning point as the lock-in thermography images.

2. The apparatus of claim 1, wherein the laser generator includes:
   a function generator generating a periodic waveform voltage in response to a trigger signal;
   a modulating driver amplifying the waveform voltage and converting the waveform voltage into a modulated current having a period of the periodic waveform voltage; and
   a laser oscillator oscillated by the modulated current thereby emitting the periodic CW laser modulated in accordance with the modulated current.

3. The apparatus of claim 2, wherein the periodic voltage includes a square waveform and the CW laser is modulated by the periodic square waveform such that the semiconductor chip undergoes periodically repeated heating and cooling at each scanning point on a surface thereof.

4. The apparatus of claim 1, wherein the laser controller includes:
   a beam expander expanding a bundle of rays of the CW laser thereby generating an expanded laser;
   a beam splitter splitting the expanded laser into a plurality of parallel spot beams as the inspection laser beam, each of the parallel spot beams having a cross-sectional beam size smaller than a surface of the semiconductor chip and at least two parallel spot beams being individually irradiated onto the surface of a single semiconductor chip; and
   a position guider changing a relative position of the beam splitter with respect to a substrate on which a plurality of the semiconductor chips is arranged, so that scanning points of the semiconductor chips to which the parallel spot beams are individually irradiated are changed by the position guider.

5. The apparatus of claim 4, wherein the beam splitter includes a plurality of beam passing holes through which the parallel spot beams individually pass toward the substrate such that the cross-sectional beam size is controlled by a hole size of the beam passing hole.

6. The apparatus of claim 5, wherein a number of the beam passing holes is three to five times of a number of the semiconductor chips on the substrate such that three to five parallel spot beams are individually irradiated onto a single semiconductor chip.

7. The apparatus of claim 4, further comprising a flat beam generator for converting a ray distribution of the expanded beam from a Gaussian distribution into a uniform distribution thereby generating a flat beam having a uniform intensity such that the parallel spot beams have the uniform intensity.

8. The apparatus of claim 4, wherein the thermal image generator includes:
 a base plate between the beam splitter and the substrate and having a plurality of penetrating holes, at least two parallel spot beams penetrating each of the penetrating holes; and
 a plurality of thermal image chips arranged on a surface of the base plate and detecting thermal waves radiated from the scanning points of the semiconductor chips, thereby generating the thermal images at each of the scanning points by a unit of the semiconductor chip.

9. The apparatus of claim 1, wherein the laser controller includes:
 a line beam generator transforming the CW laser into a linear beam as the inspection laser beam, the linear beam extending along a longitudinal direction of a substrate on which a plurality of the semiconductor chips is arranged and having a beam width that is smaller than a surface size of the semiconductor chip; and
 a beam provider providing the linear beam to a plurality of semiconductor chips arranged in the longitudinal direction such that the linear beam is simultaneously irradiated onto a plurality of scanning points of each semiconductor chip along the longitudinal direction.

10. The apparatus of claim 1, further comprising an image processor processing the lock-in amplitude images, thereby generating a surface image of each of the semiconductor chips by which the surface defect is visually displayed.

11. The apparatus of claim 10, wherein the image processor includes:
 a discontinuous image detector processing the lock-in amplitude image and detecting image singularities from the lock-in amplitude image, thereby generating a visually enhanced lock-in amplitude image in which discontinuous portions are visually shown on the lock-in amplitude image; and
 a noise filter removing noise from the visually enhanced lock-in amplitude image, thereby generating the surface image of the semiconductor chip.

12. The apparatus of claim 11, wherein the discontinuous image detector includes a holder exponent analyzer in which the image singularities are detected through a holder exponent analysis process.

13. The apparatus of claim 1, further comprising a main controller connected to the laser generator, the laser controller, the thermal image generator and the lock-in processor and wherein the main controller controls the laser generator and the thermal image generator to be synchronized with each other.

14. An apparatus for inspecting surfaces of semiconductor chips, comprising:
 a laser unit that generates a plurality of periodic continuous wave (CW) inspection laser beams;
 a wafer carrier that positions a wafer having a plurality of chips in a path of the inspection laser beams, the plurality of inspection laser beams being arranged to simultaneously heat corresponding portions of the plurality of chips, the plurality of inspection laser beams each being of a cross-sectional area that is less than a surface area of individual ones of the chips; and
 a thermal image generator detecting thermal waves radiated from the chips in response to the inspection laser beams and generating thermal images corresponding to the thermal waves,
 wherein the thermal image generator comprises:
 a base plate between the laser unit and the wafer carrier and having a plurality of penetrating holes, at least two of the inspection laser beams penetrating each of the penetrating holes; and
 a plurality of thermal image chips arranged on a surface of the base plate and detecting thermal waves radiated from the plurality of chips, thereby generating the thermal images corresponding to the plurality of chips.

15. The apparatus of claim 14 wherein the laser unit comprises:
 a laser generator that generates a first periodic continuous wave (CW) inspection laser beams; and
 a laser controller that controls a transformation of the first inspection laser beam from a single laser beam to the plurality of inspection laser beam.

16. The apparatus of claim 15 further comprising a lock-in processor processing the thermal image using a lock-in thermography technique, thereby generating a lock-in thermography image of the thermal image in which a surface defect is included.

17. The apparatus of claim 15, further comprising a main controller connected to the laser generator, the laser controller, the thermal image generator and the lock-in processor and wherein the main controller controls operation of the laser generator and the thermal image generator to be synchronized with each other.

18. The apparatus of claim 14 wherein the periodic CW laser beam causes the plurality of chips to undergo periodic heating and cooling.

* * * * *